United States Patent [19]

Monn et al.

[11] Patent Number: 5,473,077

[45] Date of Patent: Dec. 5, 1995

[54] PYRROLIDINYL DI-CARBOXYLIC ACID DERIVATIVES AS METABOTROPIC GLUTAMATE RECEPTOR AGONISTS

[75] Inventors: James A. Monn; Darryle D. Schoepp; Matthew J. Valli, all of Indianapolis, Ind.

[73] Assignee: Eli Lilly and Company, Indianapolis, Ind.

[21] Appl. No.: 337,801

[22] Filed: Nov. 14, 1994

[51] Int. Cl.$^6$ .................. C07D 207/04; C07D 403/04; C07D 403/14; A61K 31/40; A61K 31/41

[52] U.S. Cl. .................. 548/253; 548/254; 548/531; 514/381; 514/423

[58] Field of Search .................. 548/253, 254, 548/531; 514/381, 423

Primary Examiner—David B. Springer
Attorney, Agent, or Firm—Paul J. Gaylo; David E. Boone

[57] ABSTRACT

The present invention provides novel compounds that affect certain excitatory amino acid receptors, and are useful in the treatment of neurological disorders and psychiatric disorders.

30 Claims, No Drawings

PYRROLIDINYL DI-CARBOXYLIC ACID DERIVATIVES AS METABOTROPIC GLUTAMATE RECEPTOR AGONISTS

BACKGROUND OF THE INVENTION

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Annual Reviews in Pharmacology and Toxicology*, 21:165 (1981); Monaghan, Bridges, and Cotman, *Annual Reviews in Pharmacology and Toxicology*, 29:365 (1989); Watkins, Krogsgaard-Larsen, and Honore, *Transactions in Pharmaceutical Science*, 11:25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonists N-methyl-D-aspartate (NMDA), α-amino-3-hydroxy-5-methylisoxazole-4-propionic acid (AMPA), and kainic acid (KA).

The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in cAMP formation, and changes in ion channel function. Schoepp and Conn, *Trends in Pharmacological Science*, 14:13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacological Science*, 11:508 (1990); McDonald and Johnson, *Brain Research Reviews*, 15:41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

The metabotropic glutamate receptors are a highly heterogeneous family of glutamate receptors that are linked to multiple second-messenger pathways. These receptors function to modulate the presynaptic release of glutamate, and the postsynaptic sensitivity of the neuronal cell to glutamate excitation. Agonists and antagonists of these receptors are believed useful for the treatment of acute and chronic neurodegenerative conditions, and as antipsychotic, anticonvulsant, analgesic, anxiolytic, antidepressant, and antiemetic agents.

It is believed that the administration of antagonist compounds, which inhibit the activation of neural receptors, will aid in treating many of the above conditions. Particularly in cases where excitotoxicity mediates the condition, use of an antagonist compound may slow or even halt the process of neuronal cell death.

Antagonists and agonists of neural receptors are classified as selective for a particular receptor or receptor subtype, or as non-selective. Antagonists may also be classified as competitive or non-competitive. While competitive and non-competitive antagonists act on the receptors in a different manner to produce similar results, selectivity is based upon the observations that some antagonists exhibit high levels of activity at a single receptor type, and little or no activity at other receptors. In the case of receptor-specific diseases and conditions, the selective antagonists are of the most value.

A well-known selective agonist of metabotropic receptors is (1S,3R)-3-aminocyclopentane-1,3-dicarboxylic acid [(1S,3R) ACPD]. Other neurotransmitters include L-glutamate, the most abundant in situ neurotransmitter, which stimulates both the ionotropic and metabotropic classes of receptor.

To date there has been no disclosure of an agonist which is selective for a particular class or subtype of metabotropic glutamate receptor. Selective antagonists for ionotropic receptors have been disclosed, as well as general non-selective antagonists. In order to increase the therapeutic potential for the central nervous system, site-specific, selective antagonists and agonists must be developed for each of the different receptor classes and subclasses.

SUMMARY OF THE INVENTION

This invention relates to a method of treating or preventing a condition associated with an inappropriate stimulation of a glutamate receptor in a mammal which comprises administering to a mammal in need thereof an effective amount of a compound of Formula I

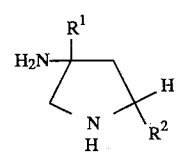

where $R^1$ and $R^2$ are independently carboxylic acid or 5-tetrazolyl, or a pharmaceutically acceptable salt or solvate thereof.

This invention also provides the novel compounds of Formula I and the salts and solvates thereof as well as pharmaceutical formulations employing a compound of Formula I, or a pharmaceutically acceptable salt or solvate thereof, in combination with one or more pharmaceutically acceptable carriers, diluents, or excipients.

DETAILED DESCRIPTION AND PREFERRED EMBODIMENTS

The terms and abbreviations used in the instant examples have their normal meanings unless otherwise designated. For example "°C" refers to degrees Celsius; "N" refers to normal or normality; "mmol" refers to millimole or millimoles; "g" refers to gram or grams; "ml" means milliliter or milliliters; "M" refers to molar or molarity; "MS" refers to mass spectrometry; "IR" refers to infrared spectroscopy; and "NMR" refers to nuclear magnetic resonance spectroscopy.

As would be understood by the skilled artisan, throughout the synthesis of the compounds of Formula I it may be necessary to employ an amino-protecting group or a carboxy-protecting group in order to reversibly preserve a reactively susceptible amino or carboxy functionality while reacting other functional groups on the compound.

Examples of such amino-protecting groups include formyl, trityl, phthalimido, trichloroacetyl, chloroacetyl, bromoacetyl, iodoacetyl, and urethane-type blocking groups such as benzyloxycarbonyl, 4-phenylbenzyloxycarbonyl, 2-methylbenzyloxycarbonyl, 4-methoxybenzyloxycarbonyl, 4- fluorobenzyloxycarbonyl, 4-chlorobenzyloxycarbonyl, 3-chlorobenzyloxycarbonyl, 2- chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl, 2-(4 -xenyl)-isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxy-carbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)-ethoxycarbonyl, 2-(methylsulfonyl)ethoxycarbonyl, 2-(triphenylphosphino)-ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalyl-methoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonlyl and the like; benzoylmethylsulfonyl group, 2-nitrophenylsulfenyl, diphenylphosphine oxide and like amino-protecting groups. The species of amino-protecting group employed is not critical so long as the derivatized amino group is stable to the condition of subsequent reaction (s) on other positions of the intermediate molecule and can be selectively removed at the appropriate point without disrupting the remainder of the molecule including any other amino-protecting group(s). Preferred amino-protecting groups are t-butoxycarbonyl (t-Boc), allyloxycarbonyl and benzyloxycarbonyl (CbZ). Further examples of these groups are found in E. Haslam, PROTECTIVE GROUPS IN ORGANIC CHEMISTRY, (J. G. W. McOmie, ed., 1973), at Chapter 2; and T. W. Greene and P. G. M. Wuts, PROTECTIVE GROUPS IN ORGANICS SYNTHESIS, (1991), at Chapter 7.

Examples of such carboxy-protecting groups include methyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, β-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl and like moieties. Preferred carboxy-protecting groups are allyl, benzyl and t-butyl. Further examples of these groups are found in E. Haslam, supra, at Chapter 5; and T. W. Greene and P. G. M. Wuts, supra, at Chapter 5.

This invention provides for compounds which are agonists of the metabotropic neural receptors in the mammalian central nervous system. The compounds have the general formula:

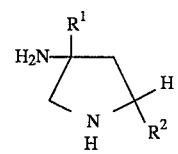

where $R^1$ and $R^2$ are independently carboxylic acid or tetrazolyl, or a pharmaceutically acceptable salt or solvate thereof.

As noted, supra, the compounds of the present invention are derivatives of pyrrolidine which are named and numbered according to the RING INDEX, The American Chemical Society, as follows.

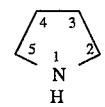

While all of the compounds of Formula I are believed to process antagonist activity at the metabotropic receptors, certain groups of Formula I compounds are more preferred for such use.

As noted supra, this invention includes the pharmaceutically acceptable salts of the compounds defined by Formula I. A compound of this invention can possess a sufficiently acidic, a sufficiently basic, or both functional groups, and accordingly react with any of a number of organic and inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenylsulfonic acid, carbonic acid, succinic acid, citric acid, benzoic, acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, γ-hydroxybutyrate, glycolate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Salts of amine groups may also comprise quarternary ammonium salts in which the amino nitrogen carries a suitable organic group such as an alkyl, alkenyl, alkynyl, or aralkyl moiety.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole.

This invention further encompasses the pharmaceutically acceptable solvates of the compounds of Formulas I. Many of the Formula I compounds can combine with solvents such as water, methanol, ethanol and acetonitrile to form pharmaceutically acceptable solvates such as the corresponding hydrate, methanolate, ethanolate and acetonitrilate.

The compounds of the present invention have multiple asymmetric centers. As a consequence of these chiral centers, the compounds of the present invention occur as racemates, mixtures of enantiomers and as individual enantiomers, as well as diastereomers and mixtures of diastereomers. All asymmetric forms, individual isomers and combinations thereof, are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in NOMENCLATURE OF ORGANIC COMPOUNDS: PRINCIPLES AND PRACTICE, (J. H. Fletcher, et al., eds., 1974) at pages 103–120.

In addition to the (R)-(S) system, the older D-L system is also used in this document to denote absolute configuration, especially with reference to amino acids or amino acid derivatives. In this system a Fischer projection formula is oriented so that the number 1 carbon of the main chain is at the top. The prefix "D" is used to represent the absolute configuration of the isomer in which the functional (determining) group is on the right side of the carbon atom at the chiral center and "L", that of the isomer in which it is on the left.

As would be expected, the stereochemistry of the Formula I compounds is critical to their potency as agonists. The relative stereo-chemistry shown in the structures is most preferred with the carboxylic acids preferably in the trans-position, and most preferably in the 2R,4R orientation. The 4-amino moiety is preferably cis with regard to the 2-carboxy group, in the preferred orientation, 4R.

The relative stereochemistry is preferably established early during synthesis, which avoids stereoisomer separation problems later in the process. Subsequent synthetic step then employ stereospecific procedures so as to maintain the preferred chiralty. The preferred methods of this invention are the methods employing those preferred compounds.

Scheme I depicted below illustrates the general process used to synthesize the intermediate compound which serves as the backbone for the compounds of this invention:

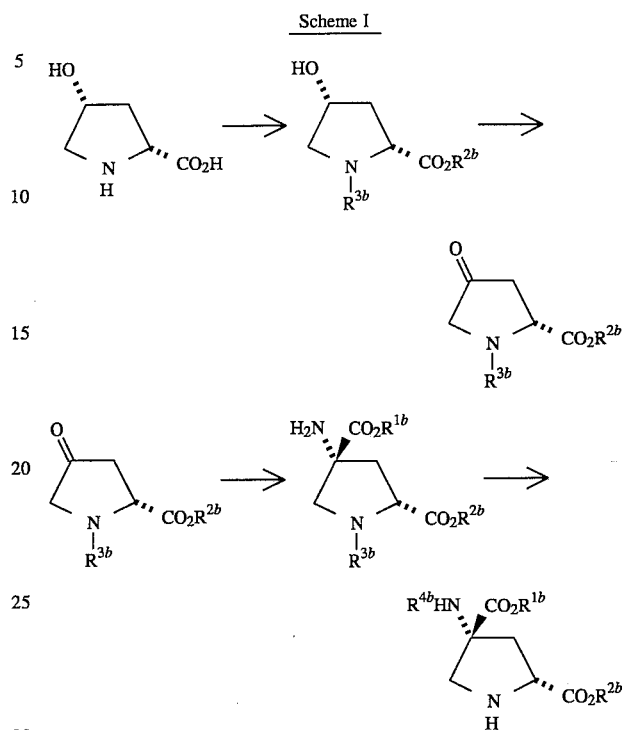

Scheme I wherein $R^{1b}$ and $R^{2b}$ are carboxy-protecting groups, and $R^{3b}$ and $R^{4b}$ are amino-protecting groups.

According to Scheme I, the preferred starting material is cis-4-hydroxy-D-proline. Though the series of reactions show, this material is converted into a carboxy- and amino-protected analog of 4-aminopyrrolidine-2,4-dicarboxylic acid. This analog is the backbone from which the preferred compounds of Formula I may be synthesized.

As shown in Scheme I, the first step of the synthesis involves the addition of the carboxy protecting group and the addition of a functional group (preferred is an aromatic analog, most preferably benzyl) to the ring nitrogen. The specific reagents and processes for adding protective groups is well-known and will be described in detail in the specific examples infra.

After protection of the 2-carboxy and ring nitrogen, the 4-hydroxy group is oxidized to an oxo group which defines the cyclic ketone intermediate shown. This intermediate is then disubstituted at the C4 position to add the 4-carboxy and 4-amino moieties. This step generally result in the formation of diastereomers at the C4 position, which are preferably separated to leave only the desired enantiomer. These 4-substituted groups are protected and the N1 moiety removed to define the final intermediate shown. Subsequent removal of the blocking groups results in the compounds of Formula I.

All specific reagents used and conditions employed in the Scheme I will be identified in the specific examples infra.

Those compounds of Formula I in which $R^1$ is tetrazolyl are prepared from the substituted 4-pyrrolidinone depicted in Scheme I, supra.

The following Preparations and Examples further illustrate the compounds of the present invention and the methods for their synthesis. The Examples are not intended to be limiting to the scope of the invention in any respect, and should not be so construed. All experiments were run under a positive pressure of dry nitrogen or argon. All solvents and reagents were purchased from commercial sources and used as received, unless otherwise indicated.

Proton nuclear magnetic resonance ($^1$H NMR) spectra were obtained on a GE QE-300 spectrometer at 300.15 MHz, a Bruker AM-500 spectrometer at 500 MHz, or a Bruker AC-200P spectrometer at 200 MHz. Free atom bombardment mass spectroscopy (FABMS) was performed on a VG ZAB-2SE instrument. Field desorption mass spectroscopy (FDMS was performed using either a VG 70SE or a Varian MAT 731 instrument.

Optical rotations were measured with a Perkin-Elmer 241 polarimeter. Chromatographic separation on a Waters Prep 500 LC was generally carried out using a linear gradient of the solvents indicated in the text unless otherwise specified.

The reactions were generally monitored for completion using thin layer chromatography (TLC). Thin layer chromatography was performed using E. Merck Kieselgel 60 $F_{254}$ plates, 5 cm×10 cm, 0.25 mm thickness. Spots were detected using a combination of UV and chemical detection (plates dipped in a ceric ammonium molybdate solution [75 g of ammonium molybdate and 4 g of cerium (IV) sulfate in 500 ml of 10% aqueous sulfuric acid] and then heated on a hot plate). Preparative centrifugal thin layer chromatography was performed on a Harrison Model 7924A Chromatotron using Analtech silica gel GF rotors.

Cation exchange chromatography was performed with Dowex® 50X8-100 ion exchange resin. Anion exchange chromatography was performed with Bio-Rad AG® 1-X8 anion-exchange resin (acetate form converted to hydroxide form). Flash chromatography was performed as described by Still, et al., *Journal of Organic Chemistry*, 43:2923 (1978).

Optical rotations are reported at the sodium-D-line (354 nm). Elemental analyses for carbon, hydrogen, and nitrogen were determined on a Control Equipment Corporation 440 Elemental Analyzer, or were performed by the Universidad Complutense Analytical Centre (Facultad de Farmacia, Madrid, Spain). Melting points were determined in open glass capillaries on a Thomas Hoover capillary melting point apparatus or a Büchi melting point apparatus, and are uncorrected.

Preparation 1

Preparation of 2R,4R-1-Benzyloxycarbonyl-4-hydroxypyrrolidine-2-carboxylic acid

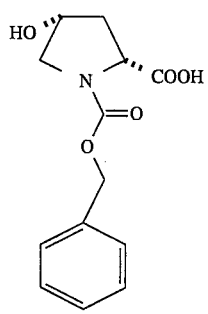

cis-4-Hydroxy-D-proline (10 g, 76.3 mmol) was dissolved in 5% aqueous sodium bicarbonate (800 ml), then a solution of benzyl chloroformate (34.1 g, 200 mmol) in toluene (400 ml) was added over a 30 minute period. The resulting reaction mixture was stirred at room temperature for 3 days. The reaction mixture was acidified with concentrated hydrochloric acid, extracted with ethyl acetate, washed with brine, dried over magnesium sulfate, and concentrated in vacuo to afford the title compound as a light yellow solid (20.42 g, 77 mmol) 100%. mp=102°–105° C. FDMS=266 M$^+$+1. $[\alpha]_D$=+125.43°.

Analysis for $C_{13}H_{15}NO_5$: Theory: C, 58.86; H, 5.70; N, 5.28. Found: C, 58.59; H, 5.65; N, 5.41.

Preparation 2

Preparation of ethyl (2R,4R)-1-benzyloxycarbonyl-4-hydroxypyrrolidine-2-carboxylate

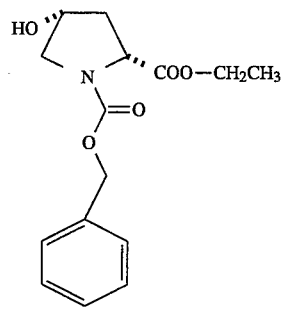

p-Toluenesulfonic acid monohydrate (1.45 g, 7.6 mmol was added to a solution of (2R,4R)-1-benzyloxycarbonyl-4-hydroxypyrrolidine-2-carboxylic acid (20.30 g, 76.5 mmol) in ethanol (100%, 1000 ml) and refluxed overnight with removal of water via a Dean-Stark trap filled with 3 Å sieves. The reaction mixture was concentrated under reduced pressure, then partitioned between a saturated sodium bicarbonate solution and ethyl acetate. The layers were separated and the aqueous phase extracted with ethyl acetate (3×500 ml). All organic phases were combined, washed with brine, dried over potassium carbonate, and concentrated in vacuo to afford the crude product which was purified by high performance liquid chromatography (10% ethyl acetate/hexanes to 50% ethyl acetate/hexanes) affording the title compound (21.25 g, 72.5 mmol) 95%. FDMS= 293 M$^+$. $[\alpha]_D$=+43.26°.

Analysis for $C_{15}H_{19}NO_5$: Theory: C, 61.42; H, 6.53; N, 4.77. Found: C, 61.29; H, 6.65; N, 4.90.

Preparation 3

Preparation of ethyl (2R,4R)-1-benzyl-4-hydroxypyrrolidine-2-carboxylate

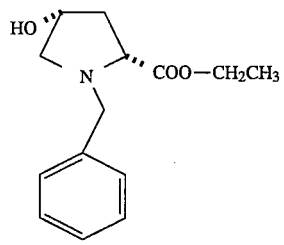

Ethyl (2R,4R)-1-benzyloxycarbonyl-4-hydroxypyrrolidine-2-carboxylate (21.15 g, 72.1 mmol) was added to an ethanolic suspension of 5% palladium on activated carbon (4.5 g in 275 ml) and exposed to hydrogen gas (60 psi) at room temperature for 2.5 hours. The reaction mixture was filtered through CELITE® and concentrated in vacuo no yield the crude product (11.27 g, 71 mmol, 98%). The crude product was reconstituted in methylene chloride (200 ml), treated with N,N-diisopropylethylamine (18.10 g, 140 mmol), and then benzyl bromide (14.38 g, 84 mmol) in methylene chloride (100 ml) was added dropwise. Upon complete addition the resulting reaction mixture was stirred at room temperature overnight. water (100 ml) was added to the reaction mixture and the product extracted with diethyl ether (3×250 ml). All organic phases were combined, washed with brine, dried over potassium carbonate, and concentrated in vacuo to yield the crude product which was purified by HPLC (10% ethyl acetate/hexanes to 50% ethyl acetate/hexanes) affording the title compound (12.35 g, 50 mmol) 71%. FDMS=249 M$^+$. $[\alpha]_D$=+167.68°

Analysis for $C_{14}H_{19}NO_3$.0.4 water: Theory: C, 65.55; H, 7.78; N, 5.46. Found: C, 65.70; H, 7.64; N, 5.46.

Preparation 4

Preparation of Ethyl (2R)-1-benzyl-4-oxopyrrolidine-2-carboxylate

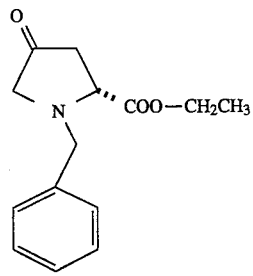

Oxalyl chloride (16.0 g, 126 mmol, 11 ml) was added dropwise to a solution of anhydrous methylene chloride (300 ml) and dimethylsulfoxide (13.12 g, 168 mmol) at −78° C. The reaction mixture was allowed to equilibrate for 10 minutes, after which time a solution of ethyl (2R,4R)-1-benzyl-4-hydroxypyrrolidine-2-carboxylate (20.90 g, 84 mmol) in methylene chloride (100 ml) was added dropwise at a rate to keep the reaction temperature below −60° C. Upon complete addition the reaction mixture was allowed to stir at −78° C. for 2 hours, then triethylamine (25.50 g, 252 mmol) was added dropwise. After complete addition, the reaction was allowed to warm to room temperature. Water (50 ml) was added to the reaction mixture, the pH was adjusted to 10 with sodium bicarbonate, and the product extracted with diethyl ether (3×200 ml). All organic phases were combined, washed with brine, dried over potassium carbonate, and concentrated in vacuo to yield crude product which was purified by high performance liquid chromatography (10% ethyl acetate/hexanes to 50 % ethyl acetate/hexanes) affording the title compound (20.44 g, 82.7 mmol) 98%. FDMS=247 M$^+$. $[\alpha]_{589}$=+31.10°.

Analysis for $C_{14}H_{17}NO_3$: Theory: C, 68.00; H, 6.93; N, 5.66. Found: C, 67.76; H, 6.91; N, 5.65.

Preparation 5

Preparation of diethyl (2R,4R)-1-benzyl-4-aminopyrrolidine-2,4-dicarboxylate

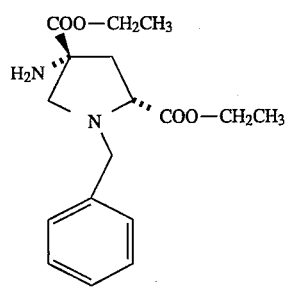

Potassium cyanide (13.36 g, 205 mmol) was added in one portion to a solution of ethyl (2R)-1-benzyl-4-oxopyrrolidine-2-carboxylate (20.30 g, 82 mmol) and ammonium carbonate (19.21 g, 246 mmol), in ethanol (500 ml) and water (500 ml). The resulting reaction mixture was heated at 55° C. for 2 days. Sodium hydroxide (90.0 g, 2.25 mol) was added and the reaction was warmed under refluxed overnight. The reaction mixture was chilled to 0° C., acidified to pH 1 with concentrated hydrochloric acid (~200 ml), and concentrated in vacuo. Ethanol (500 ml) was added to the crude amino diacid mixture and then concentrated to dryness (5×), so as to remove residual water. The resulting anhydrous amino diacid was then reconstituted in ethanol (1 L), cooled to 0° C., and treated with thionyl chloride (39.02 g, 328 mmol). Upon complete addition the reaction mixture was refluxed for three days. The solids were filtered and the filtrate was concentrated in vacuo. The crude product was partitioned between 3N sodium hydroxide, sodium chloride, and ethyl acetate. The ethyl acetate was removed and the aqueous phase extracted with ethyl acetate (3×1 L). All the organic phases were combined, washed with brine, dried over potassium carbonate and concentrated in vacuo to yield a dark red oil, which was purified by HPLC (10% ethyl acetate/hexanes to 90% ethyl acetate/hexanes) affording the title compound (12.14 g, 38 mmol) 46%. FDMS=320 M$^+$. $[\alpha]_D$=+203.29°.

Analysis for $C_{17}H_{24}N_2O_4$: Theory: C, 63.73; H, 7.55; N, 8.74. Found: C, 63.74; H, 7.64; N, 8.50.

Preparation 6

Preparation of diethyl (2R,4R)-1-benzyl-4-(tert-butyloxycarbonylamino)pyrrolidine-2,4-dicarboxylate

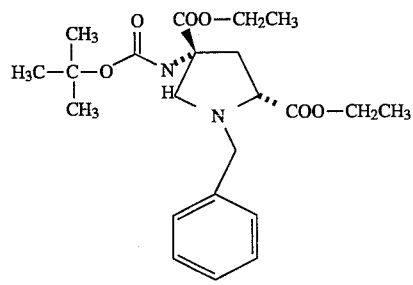

Di-tert-butyl-dicarbonate (12.26 g, 56.2 mmol) was added in one portion to a solution of diethyl (2R,4R)-1-benzyl-4-aminopyrrolidine-2,4-dicarboxylate (12.0 g, 37.5 mmol) in methylene chloride (400 ml) and the resulting reaction mixture was stirred at room temperature overnight. Sodium hydroxide (100 ml of a 0.5N solution) was added to the reaction mixture and the product extracted with diethyl ether. All the organic phases were combined, washed with brine, dried over potassium carbonate, and concentrated in vacuo to yield the crude product, which was purified by high performance liquid chromatography (10% ethyl acetate/hexanes to 50% ethyl acetate/hexanes) affording the title compound (15.92 g, 37.5 mmol), 100%. FDMS=420 M⁺. $[\alpha]_D=+99.04°$.

Analysis for $C_{22}H_{32}N_2O_6$: Theory: C, 62.84; H, 7.67; N, 6.66. Found: C, 63.06; H, 7.58; N, 6.51.

Preparation 7

Preparation of diethyl (2R,4R)-4-(tert-butyloxycarbonylamino)pyrrolidine-2,4-dicarboxylate

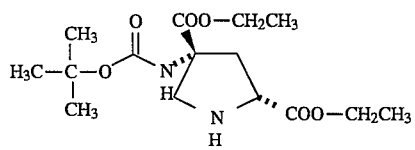

Diethyl (2R,4R)-1-benzyl-4-(tert-butyloxycarbonylamino)pyrrolidine-2,4-dicarboxylate (15.80 g, 37.5 mmol) was added to an ethanolic suspension (100 mL) of 5% Pd/C (4.0 g) and exposed to hydrogen gas (60 psi) for 4 hours at room temperature. The reaction mixture was filtered through CELITE® and concentrated in vacuo to yield the crude product, which was purified by high performance liquid chromatography (20% ethyl acetate/hexanes to 80% ethyl acetate/hexanes) affording the title compound (10.48 g, 31.7 mmol) 85%. mp=58°–60° C.

FDMS=331 M⁺+1. $[\alpha]_D=+10.63°$.

Analysis for $C_{15}H_{26}N_2O_6$: Theory: C, 54.53; H, 7.93; N, 8.48. Found: C, 54.29; H, 7.79; N, 8.42.

EXAMPLE 1

Preparation of (2R,4R) 4-aminopyrrolidine-2,4-dicarboxylic acid

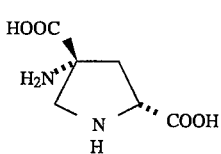

A solution of 2R,4R-Diethyl 4-(tert-butyloxycarbonylamino)pyrrolidine-2,4-dicarboxylate (1.00 g, 3.00 mmol) in diethyl ether (35 ml) was chilled to 0° C., purged with anhydrous hydrogen chloride gas, and allowed to warm to room temperature as it stirred for one hour. The reaction mixture was concentrated to dryness, and stirred in a 1:1 mixture of tetrahydrofuran/1N sodium hydroxide (20 ml total volume) at room temperature overnight. The reaction mixture was neutralized, concentrated to dryness, reconstituted in water and adjusted to pH 2 with 1N hydrochloric acid, and purified by cation exchange chromatography (5% pyridine/water) affording the title compound (0.40 g, 2.30 mmol) 77%. mp=>250° C.

FDMS=315 M⁺+1. $[\alpha]_D=+93.16°$.

Analysis for $C_6H_{10}N_2O_4$: Theory: C, 41.38; H, 5.79; N, 16.08. Found: C, 41.23; H, 5.78; N, 15.87.

The Formula I compounds of the present invention are agonists of certain metabotropic excitatory amino acid receptors. Specifically, the Formula I compounds are agonists of the negatively-coupled cAMP-linked metabotropic glutamate receptors. Therefore, another aspect of the present invention is a method of affecting an excitatory amino acid receptor in mammals, which comprises administering to a mammal requiring modulated excitatory amino acid neurotransmission a pharmacologically-effective amount of a compound of Formula I. The term "pharmacologically-effective amount" is used to represent an amount of the compound of the invention which is capable of affecting the excitatory amino acid receptors. By affecting, a compound of the invention is acting as an agonist. When a compound of the invention acts as an agonist, the interaction of the compound with the excitatory amino acid receptor mimics the response of the interaction of this receptor with its natural ligand (i.e. L-glutamate).

The particular dose of compound administered according to this invention will, of course, be determined by the particular circumstances surrounding the case, including the compound administered, the route of administration, the particular condition being treated, and similar considerations. The compounds can be administered by a variety of routes including oral, rectal, transdermal, subcutaneous, intravenous, intramuscular, or intranasal routes. Alternatively, the compound may be administered by continuous infusion. A typical daily dose will contain from about 0.001 mg/kg to about 100 mg/kg of the active compound of this invention. Preferably, daily doses will be about 0.05 mg/kg to about 50 mg/kg, more preferably from about 0.1 mg/kg to about 20 mg/kg.

A variety of physiological functions have been shown to be subject to influence by excessive or inappropriate stimulation of excitatory amino acid transmission. The Formula I compounds of the present invention are believed to have the ability to treat a variety of neurological disorders in mammals associated with this condition, including acute neurological disorders such as cerebral deficits subsequent to cardiac bypass surgery and grafting, cerebral ischemia (e.g. stroke and cardiac arrest), spinal cord trauma, head trauma, perinatal hypoxia, and hypoglycemic neuronal damage. The Formula I compounds are believed to have the ability to treat a variety of chronic neurological disorders, such as Alzheimer's disease, Huntington's Chorea, amyotrophic lateral sclerosis, AIDS-induced dementia, ocular damage and retinopathy, cognitive disorders, and idopathic and drug-induced Parkinson's. The present invention also provides methods for treating these disorders which comprises administering to a patient in need thereof an effective amount of a compound of Formula I.

The Formula I compounds of the present invention are also believed to have the ability to treat a variety of other neurological disorders in mammals that are associated with glutamate dysfunction, including muscular spasms, convulsions, migraine headaches, urinary incontinence, psychosis, drug tolerance, withdrawal, and cessation (i.e. opiates, benzodiazepines, nicotine, cocaine, or ethanol), smoking cessation, anxiety and related disorders (e.g. panic attack), emesis, brain edema, chronic pain, sleep disorders, Tourette's syndrome, attention deficit disorder, and tardive dyskinesia. Therefore, the present invention also provides methods for treating these disorders which comprise administering to a patient in need thereof an effective amount of the compound of Formula I.

The compounds of the present invention are agonists of cAMP-linked metabotropic glutamate receptors. These compounds are negatively coupled through the receptor to adenyl cyclase, inhibiting the formation of cyclic adenosine monophosphate. The Formula I compounds of the present invention are, therefore, believed to have the ability to treat a variety of psychiatric disorders, such as schizophrenia, anxiety and related disorders (e.g. panic attack), depression, bipolar disorders, psychosis, and obsessive compulsive disorders. The present invention also provides methods for treating these disorders which comprises administering to a patient in need thereof an effective amount of a compound of Formula I.

The affinity of the compounds for metabotropic glutamate receptors was demonstrated by the selective displacement of (1S,3R)-1-aminocyclopentane-1,3-dicarboxylic acid-sensitive [$^3$H]glutamate binding to rat brain cell membranes. The binding of [$^3$H]glutamate ([$^3$H]Glu) was conducted with crude membranes of rat forebrain as described by Schoepp and True. Schoepp and True, *Neuroscience Letters*, 145:100–104 (1992); Wright, et al., *Journal of Neurochemistry*, 63:938–945 (1994).

In addition to the binding assays described supra, representative compounds of Formula I were also tested for their ability to affect the cAMP-linked metabotropic glutamate receptors. These compounds were tested for their ability to decrease forskolin-stimulated cAMP formation in the ram hippocampus and the rat cerebral cortex, using the procedures described in Schoepp and Johnson. Schoepp and Johnson, *Neurochem. Int.*, 22:277–283 (1993). Those compounds tested did decrease this cAMP formation.

Functional Assays Employing Cloned Subtypes of Metabotropic Receptor

The appropriate functional assay using recombinant metabotropic glutamate receptors, adenylate cyclase activity or phosphatidylinositol hydrolysis, is performed substantially as before using standard procedures.

(a) Adenylate Cyclase Activity.

Adenylate cyclase activity is determined in initial experiments in transfected mammalian cells, using standard techniques. See, e.g., N. Adham, et al., supra,; R. L. Weinshank, et al *Proceedings of the National Academy of Sciences (USA)*, 89:3630–3634 (1992), and the references cited therein.

Mammalian cells (the cell line AV12-664 is especially preferred) are stably transfected with a plasmid comprising the cloned metabotropic glutmate receptor. The cells are maintained in a medium consisting of Dulbecco's Modified Eagle's Medium (DMEM) containing 5% dialyzed fetal calf serum, 10 mM HEPES buffer (pH 7.3), 1 mM sodium pyruvate, 1 mM glutamine, and 200 µg/ml hygromycin.

For the assay the cells are disassociated from stock culture flasks with trypsin, and planted in 24-well plastic culture dishes (15 mm wells) at a density of 500,000–700,000 cells per well using the same culture medium. After twenty four hours incubation in a humidified carbon dioxide incubator, the cell monolayers are washed with buffer (Dulbecco's phosphate-buffered saline containing 0.5 mM isobutylmethylxanthine and 3 mM glucose) and then incubated in the same buffer at 37° C. for 30 minutes. The monolayers are then washed six additional times with buffer.

Drugs and forskolin, or forskolin alone, dissolved in buffer, are added after the final wash. After incubating for 20 minutes at 37° C., 0.5 ml of 8 mM EDTA is added to each well. The plates are then placed in a boiling water bath fox about four minutes. The supernatant fluids are then recovered from the wells and lyophilized. Cyclic adenosinemonophosphate determinations are carried out on the lyophilized samples using commercially available radioimmunoassay kits, following the manufacturer's instructions. The cAMP level in wells containing drug are the compared to the forskolin controls.

(b) Phosphatidylinositol Assay

Phosphatidylinositol hydrolysis in clonal cell lines of AV12 harboring a plamid expressing the cloned metabotropic glutamate receptor is measured in response to glutamate agonists as a functional assay for metabotropic glutamate receptor activity according to D. Schoepp, *Trends in Pharmaceutical Sciences*, 11:508 (1990).

Twenty-four-well tissue-culture vessels are seeded with approximately 250,000 cells per well in Dulbecco's Minimal Essential Media (D-MEM) (in the absence of glutamic acid) which contained 2 mM glutamine and 10% dialyzed fetal calf serum. After 24 hours growth at 37° C. the media is removed and replaced with fresh media containing four microcuries of [$^3$H]myoinositol per well and the cultures are incubated a further 16 to 20 hours. The media is then removed and the cells in each well are washed with serum free medium containing 10 mM lithium chloride, 10 mM myoinositol, and 10 mM HEPES (2×1 ml washes). After the final wash, 0.5 ml of washing solution is added containing the appropriate concentrations of drugs and vehicles.

If the particular assay is also testing antagonists, a ten minute incubation is performed prior to agonist induction. Cells are incubated for about one hour at 37° C. in 95%:5% $O_2$:$CO_2$ or as appropriate for time course. The reactions are terminated by removing media and adding 1 ml of cooled 1:1 acetone:methanol followed by induction on ice for a minimum of twenty minutes.

These extracts are then removed and placed in 1.5 ml centrifuge tubes. Each well is washed with 0.5 ml water and this wash is added to the appropriate extract. After mixing and centrifugation, each aqueous supernatant is processed by chromatography on a QMA SEP-PAK® column, which had previously been wetted and equilibrated by passing 10 ml of water, followed by 8 ml of 1M triethylammonium hydrogen carbonate (TEAB), followed by 10 ml of water through the column.

The assay supernatants contining the water soluble [$^3$H] inositol phosphate are passed over the columns. This is followed by a 10 ml water wash and a 4 ml wash with 0.02M TEAB to remove [$^3$H]inositol precursors. [$^3$H]Inositol phosphate is eluted with 4 ml of 0.1M TEAB into scintillation vials and counted in the presence of scintillation cocktail. Total protein in each sample is measured using standard techniques. Assays are measured as the amount of [$^3$H] inositol phosphate release per milligram of protein.

These types of assay, employing different subtypes of cloned metabotrapic receptors, may be used to determine which compounds have selective affinity in that they bind to one subtype of receptor with a greater affinity than another subtype. In performing such experiments with some of the compounds of the present invention, it has been demonstrated that some compounds of the present invention act as agonists with the cAMP-linked metabotropic glutamate receptors, while showing less activity with the phosphatidylinositol-linked metabotropic glutamate receptors.

The compounds of Formula I are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

The present invention also includes pharmaceutical compositions which contain, as an active ingredient, a compound of Formula I associated with pharmaceutically acceptable carriers. In making the compositions of the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Example 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| Active Ingredient | 5 |
| Lactose | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50°–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Capsules, each containing 15 mg of medicament, are made as follows:

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Example 9

An intravenous formulation may be prepared as follows:

| Ingredient | Quantity |
| --- | --- |
| Active Ingredient | 250.0 mg |
| Isotonic saline | 1000 ml |

Formulation Example 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

Sublingual or buccal tablets, each containing 10 mg of active ingredient, may be prepared as follows:

| Ingredient | Quantity Per Tablet |
| --- | --- |
| Active Ingredient | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50°–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

We claim:

1. A compound of the formula

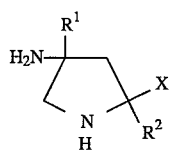

where $R^1$ and $R^2$ are independently carboxylic acid or 5-tetrazolyl, or a pharmaceutically acceptable salt or solvate thereof.

2. A compound as claimed in claim 1 wherein $R^1$ is carboxylic acid, or a pharmaceutically acceptable salt or solvate thereof.

3. A compound as claimed in claim 2 wherein $R^2$ is carboxylic acid, or a pharmaceutically acceptable salt or solvate thereof.

4. A compound as claimed in claim 3 that is (2R,4R) 4-aminopyrrolidine-2,4-dicarboxylic acid, (2S,4S) 4-aminopyrrolidine-2,4-dicarboxylic acid, or (2R,4S) 4-aminopyrrolidine-2,4-dicarboxylic acid, or a pharmaceutically acceptable salt or solvate thereof.

5. The compound as claimed in claim 4 that is (2R,4R) 4-aminopyrrolidine-2,4-dicarboxylic acid, or a pharmaceutically acceptable salt or solvate thereof.

6. A compound as claimed in claim 1 wherein $R^1$ is 5-tetrazolyl, or a pharmaceutically acceptable salt or solvate thereof.

7. A compound as claimed in claim 6 wherein $R^2$ is 5-tetrazolyl, or a pharmaceutically acceptable salt or solvate thereof.

8. A compound as claimed in claim 7 that is (2R,4R) 4-amino-2,4-di(tetrazol-5-yl)pyrrolidine, (2S,4S) 4-amino-2,4-di(tetrazol-5-yl)pyrrolidine, or (2R,4S) 4-amino-2,4-di(tetrazol-5-yl)pyrrolidine, or a pharmaceutically-acceptable salt or solvate thereof.

9. The compound as claimed in claim 8 that is (2R,4R) 4-amino-2,4-di(tetrazol-5-yl)pyrrolidine, or a pharmaceutically acceptable salt or solvate thereof.

10. A method for treating a neurological disorder in a mammal which comprises administering to a mammal in need thereof a pharmaceutically-effective amount of a compound of the formula

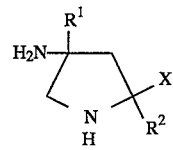

where $R^1$ and $R^2$ are independently carboxylic acid or 5-tetrazolyl, or a pharmaceutically acceptable salt or solvate thereof.

11. A method as claimed in claim 10 wherein said neurological disorder is mediated through a cAMP-linked metabotropic glutamate receptors.

12. A method as claimed in claim 11 wherein said neurological disorder is mediated through a mGluR2 receptor.

13. A method as claimed in claim 10 employing a compound wherein $R^1$ is carboxylic acid, or a pharmaceutically acceptable salt or solvate thereof.

14. A method as claimed in claim 13 employing a compound wherein $R^2$ is carboxylic acid, or a pharmaceutically acceptable salt or solvate thereof.

15. A method as claimed in claim 14 employing a compound that is (2R,4R) 4-aminopyrrolidine-2,4-dicarboxylic acid, (2S,4S) 4-aminopyrrolidine-2,4-dicarboxylic acid, or (2R,4S) 4-aminopyrrolidine-2,4-dicarboxylic acid, or a pharmaceutically acceptable salt or solvate thereof.

16. A method as claimed in claim 15 employing (2R,4R) 4-aminopyrrolidine-2,4-dicarboxylic acid, or a pharmaceutically acceptable salt or solvate thereof.

17. A method as claimed in claim 15 employing (2S,4S) 4-aminopyrrolidine-2,4-dicarboxylic acid, or a pharmaceutically acceptable salt or solvate thereof.

18. A method as claimed in claim 10 employing a compound wherein $R^1$ is 5-tetrazolyl, or a pharmaceutically acceptable salt or solvate thereof.

19. A method as claimed in claim 18 employing a compound wherein $R^2$ is 5-tetrazolyl, or a pharmaceutically acceptable salt or solvate thereof.

20. A method as claimed in claim 19 employing a compound that is (2R,4R) 4-amino-2,4-di(tetrazol-5-yl)pyrrolidine, (2S,4S) 4-amino-2,4-di(tetrazol-5-yl)pyrrolidine, or (2R,4S) 4-amino-2,4-di(tetrazol-5-yl)pyrrolidine, or a pharmaceutically acceptable salt or solvate thereof.

21. A method as claimed in claim 20 employing (2R,4R) 4-amino-2,4-di(tetrazol-5-yl)pyrrolidine, or a pharmaceutically acceptable salt or solvate thereof.

22. A pharmaceutical formulation comprising an effective amount of a compound of the formula

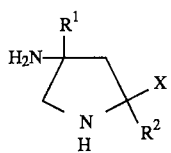

where $R^1$ and $R^2$ are independently carboxylic acid or 5-tetrazolyl, or a pharmaceutically acceptable salt or solvate thereof, in combination with one or more pharmaceutically acceptable carriers, diluents, or excipients therefor.

23. A pharmaceutical formulation as claimed in claim 22 employing a compound wherein $R^1$ is carboxylic acid, or a pharmaceutically acceptable salt or solvate thereof.

24. A pharmaceutical formulation as claimed in claim 23 employing a compound wherein $R^2$ is carboxylic acid, or a pharmaceutically acceptable salt or solvate thereof.

25. A pharmaceutical formulation as claimed in claim 24 employing a compound that is (2R,4R) 4-aminopyrrolidine-2,4-dicarboxylic acid, (2S,4S) 4-aminopyrrolidine-2,4-dicarboxylic acid, or (2R,4S) 4-aminopyrrolidine-2,4-dicarboxylic acid, or a pharmaceutically acceptable salt or solvate thereof.

26. A pharmaceutical formulation as claimed in claim 25 employing (2R,4R) 4-aminopyrrolidine-2,4-dicarboxylic acid, or a pharmaceutically acceptable salt or solvate thereof.

27. A pharmaceutical formulation as claimed in claim 24 employing a compound wherein $R^1$ is 5-tetrazolyl, or a pharmaceutically acceptable salt or solvate thereof.

28. A pharmaceutical formulation as claimed in claim 27 employing a compound wherein $R^2$ is 5-tetrazolyl, or a pharmaceutically acceptable salt or solvate thereof.

29. A pharmaceutical formulation as claimed in claim 28 employing a compound that is (2R,4R) 4-amino-2,4-di(tetrazol-5-yl)pyrrolidine, (2S,4S) 4-amino-2,4-di(tetrazol-5-yl)pyrrolidine, or (2R,4S) 4-amino-2,4-di(tetrazol-5-yl)pyrrolidine, or a pharmaceutically acceptable salt or solvate thereof.

30. A pharmaceutical formulation as claimed in claim 29 employing (2R,4R) 4-amino-2,4-di(tetrazol-5-yl)pyrrolidine, or a pharmaceutically acceptable salt or solvate thereof.

* * * * *

UNITED STATES PATENT AND TRADEMARK OFFICE
CERTIFICATE OF CORRECTION

PATENT NO. : 5,473,077

DATED : December 5, 1995

INVENTORS : James A. Monn, et. al.

It is certified that an error appears in the above-identified patent and that said Letters Patent is hereby corrected as shown below:

Col. 19, lines 40 to 46, the chemical structure should be as follows:

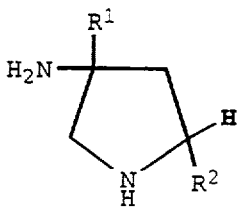

instead of

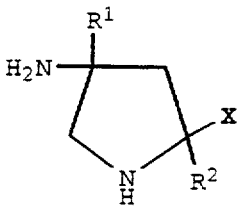

Col. 20, line 7 should read "di(tetrazol-5-yl)pyrrolidine, or a pharmaceutically accept-" instead of "di(tetrazol-5-yl)pyrrolidine, or a pharmaceutically-accept-"

Col. 20, lines 17 to 24, the chemical structure should be as follows:

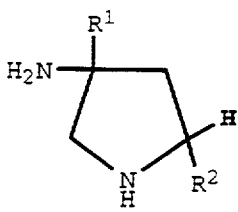

instead of

UNITED STATES PATENT AND TRADEMARK OFFICE
CERTIFICATE OF CORRECTION

PATENT NO. : 5,473,077  Page 2 of 3
DATED : Dec. 5, 1995
INVENTOR(S) : James A. Monn, et al.

It is certified that error appears in the above-indentified patent and that said Letters Patent is hereby corrected as shown below:

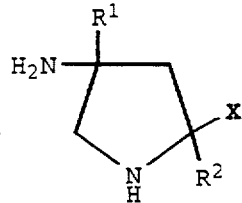

Col. 21, lines 1 to 8, the chemical structure should be

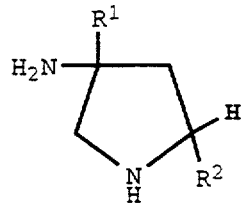

UNITED STATES PATENT AND TRADEMARK OFFICE
CERTIFICATE OF CORRECTION

PATENT NO. : 5,473,077

DATED : Dec. 5, 1995

INVENTOR(S) : James A. Monn, et al.

It is certified that error appears in the above-indentified patent and that said Letters Patent is hereby corrected as shown below:

instead of

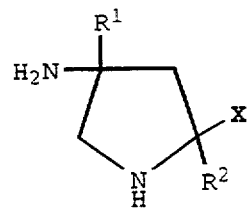

Signed and Sealed this

Twenty-third Day of July, 1996

Attest:

BRUCE LEHMAN

Attesting Officer　　　Commissioner of Patents and Trademarks